United States Patent [19]

Hofer et al.

[11] 4,190,652
[45] Feb. 26, 1980

[54] COMBATING PESTS WITH O-PHENYL-THIONOTHIOLALKANEPHOSPHONIC ACID ESTERS

[75] Inventors: Wolfgang Hofer; Fritz Maurer; Hans-Jochem Riebel, all of Wuppertal; Rolf Schröder, Velbert; Bernhard Homeyer, Leverkusen; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 885,234

[22] Filed: Mar. 10, 1978

[30] Foreign Application Priority Data

Apr. 2, 1977 [DE] Fed. Rep. of Germany ....... 2714771

[51] Int. Cl.$^2$ .......................... A01N 9/36; C07F 9/40
[52] U.S. Cl. .................................. 424/222; 260/940; 260/941; 260/949; 260/951; 260/954; 260/961; 424/210; 424/212; 424/216; 424/217; 424/218
[58] Field of Search ............... 260/961, 940, 951, 949, 260/954

[56] References Cited

U.S. PATENT DOCUMENTS

| 2,988,474 | 6/1961 | Szabo et al. | 260/961 X |
| 3,209,020 | 9/1965 | Schrader | 260/961 X |
| 3,361,855 | 1/1968 | Schrader | 260/961 |

FOREIGN PATENT DOCUMENTS

| 1954894 | 5/1971 | Fed. Rep. of Germany | 260/940 |
| 48-98037 | 12/1973 | Japan | 260/961 |

Primary Examiner—Anton H. Sutto
Attorney, Agent, or Firm—Sprung, Felfe, Horn, Lynch & Kramer

[57] ABSTRACT

O-Phenyl-thionothiolalkanephosphonic acid esters of the formula

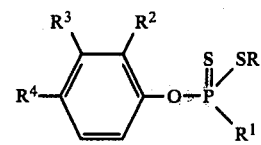

wherein
R is alkyl, halogenoalkyl, alkenyl or alkynyl,
$R^1$ is alkyl, and
$R^2$, $R^3$ and $R^4$ each independently is hydrogen, halogen, cyano, alkyl, alkylthio, alkylsulphonyl, alkoxy, nitro, carbalkoxy or phenyl,
which possess arthropodicidal and nematicidal properties.

14 Claims, No Drawings

COMBATING PESTS WITH O-PHENYL-THIONOTHIOLALKANEPHOSPHONIC ACID ESTERS

The present invention relates to and has for its objects the provision of particular new O-phenyl-thionothiolalkanephosphonic acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is already known that O-halogenophenyldithiophosphonic acid esters, for example O-(2,4-dichlorophenyl)-S-n-propyl-thionothiol-methane- and -ethane-phosphonic acid ester and O-(3-chlorophenyl)-S-cyanomethylthionothiol-ethane-phosphonic acid ester, possess insecticidal and acaricidal properties (see Japanese Patent Specification No. 48-98,037 and German Offenlegungsschrift (German Published Specification) No. 1,954,894).

The present invention now provides, as new compounds, the O-phenyldithiophosphonic acid esters of the general formula

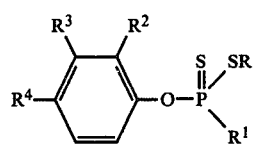 (I), in which
R represents alkyl, halogenoalkyl, alkenyl or alkynyl,
$R^1$ represents alkyl and
$R^2$, $R^3$ and $R^4$, which need not be identical, each represent hydrogen, halogen, cyano, alkyl, alkylthio, alkylsulphonyl, alkoxy, nitro, carbalkoxy or phenyl.

These new compounds are distinguished by powerful insecticidal, acaricidal and nematicidal properties.

Preferably, R represents straight-chain or branched alkyl with 1 to 6 (especially 1 to 4) carbon atoms, straight-chain or branched alkenyl or alkynyl each with up to 6 (especially with up to 4) carbon atoms or straight-chain or branched halogenoalkyl (especially chloroalkyl) with 1 to 6 (especially 1 to 4) carbon atoms, $R^1$ represents straight-chain or branched alkyl with 1 to 6 (especially 1 to 4) carbon atoms, $R^2$ represents hydrogen, cyano, nitro, chlorine, bromine, phenyl, straight-chain or branched alkyl with 1 to 4 carbon atoms, carbalkoxy with 1 to 4 carbon atoms in the alkoxy radical, or straight-chain or branched alkoxy or alkylthio each with 1 to 4 carbon atoms, $R^3$ represents hydrogen, chlorine, methoxy or ethoxy, and $R^4$ represents hydrogen, chlorine, cyano, nitro, methoxy, ethoxy, methylthio, ethylthio, methylsulphonyl, ethylsulphonyl or straight-chain or branched alkyl with 1 to 4 carbon atoms.

Particularly preferred compounds of the formula (I) are those in which (a) $R^2$, $R^3$ and $R^4$ are identical and represent hydrogen,
(b) $R^2$ has the meaning stated above to be preferred and $R^3$ and $R^4$ each represent hydrogen,
(c) $R^3$ has the meaning stated above to be preferred and $R^2$ and $R^4$ each represent hydrogen,
(d) $R^4$ has the meaning stated above to be preferred and $R^2$ and $R^3$ each represent hydrogen or
(e) $R^2$ and $R^4$ are identical and represent chlorine or methyl and $R^3$ represents hydrogen.

Surprisingly, the O-phenyl-dithiophosphonic acid esters according to the invention have a better insecticidal, acaricidal and nematicidal action than the O-halogenophenyldithiophosphonic acid esters of analogous structure and of the same type of action, which were previously known from the literature. The compounds according to the present invention thus represent a genuine enrichment of the art.

The invention also provides a process for the preparation of an O-phenyldithiophosphonic acid ester (I) in which (A) a dithioalkanephosphonic acid monoester halide of the general formula

 (II), in which
R and $R^1$ have the above-mentioned meanings and
Hal represents halogen, preferably chlorine, is reacted, if appropriate in the presence of a solvent or diluent, with a phenol of the general formula

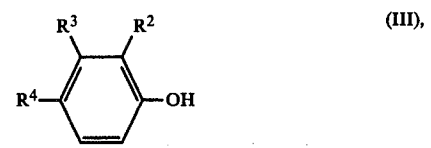 (III), in which
$R^2$, $R^3$ and $R^4$ have the above-mentioned meanings, the latter being employed in the form of an alkali metal salt, alkaline earth metal salt or ammonium salt or as such in the presence of an acid acceptor, or (B) an O-aryldithio-alkanephosphonic acid monoester of the general formula

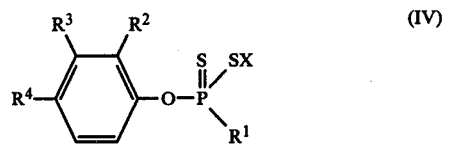 (IV)

in which
$R^1$, $R^2$, $R^3$ and $R^4$ have the above-mentioned meanings and
X represents hydrogen or one equivalent of an alkali metal or alkaline earth metal,
is reacted with a halide of the general formula

 (V), in which
R has the above-mentioned meaning and
$Hal^1$ represents halogen, preferably chlorine or bromine,
if appropriate in the presence of an acid acceptor and, if appropriate, in the presence of a solvent or diluent, or (C) an O-arylthionoalkanephosphonic acid monoester halide of the general formula

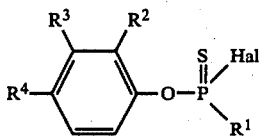

in which

R¹, R², R³, R⁴ and Hal have the above-mentioned meanings,
is reacted, if appropriate in the presence of a solvent or diluent, with a mercaptan of the general formula

HSR       (VII), in which

R has the above-mentioned meaning, the latter being employed as such, in the presence of an acid acceptor, or in the form of an alkali metal salt or alkaline earth metal salt.

If, for example, following process variant (A), S-methyl-thionothiol-ethanephosphonic acid monoester chloride and 4-ethyl-sulphonyl-phenol, or, following process variant (B), the potassium salt of O-(2,4-dibromophenyl)-thionothiolethane-phosphonic acid ester and iso-propyl bromide, or following process variant (C), O-(3-cyanophenyl)-thiono-n-propane-phosphonic acid monoester chloride and n-butyl-mercaptan, are used as the starting materials, the course of the reactions can be represented by the following equations:

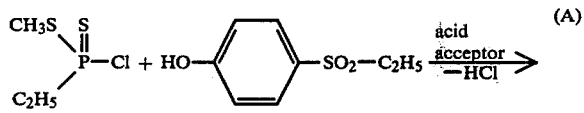

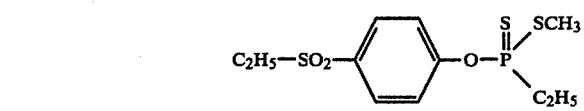

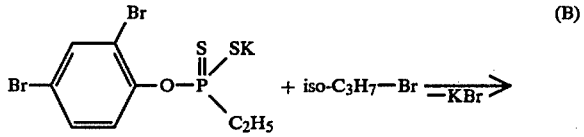

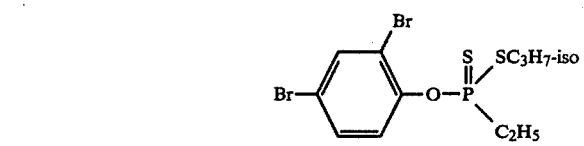

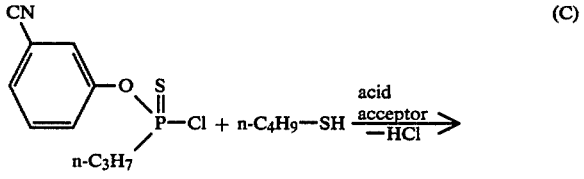

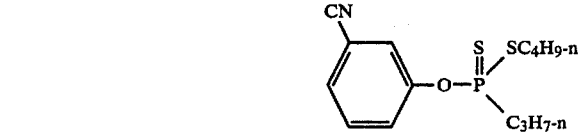

The dithioalkanephosphonic acid monoester halides (II) to be used as starting materials have been described in the literature in the majority of cases; they all can be prepared according to processes known from the literature (see, for example U.S.S.R. Patent Specification No. 187,797 and U.S. Pat. No. 3,489,825).

The following may be mentioned as specific examples thereof: S-methyl-methane-, S-ethyl-methane-, S-n-propyl-methane-, S-iso-propyl-methane-, S-n-butyl-methane-, S-iso-butyl-methane-, S-sec.-butyl-methane-, S-tert.-butyl-methane-, S-allyl-methane-, S-propenyl-methane-, S-but-2-enyl-methane-, S-but-3-enyl-methane-, S-propynyl-methane-, S-but-1-ynyl-methane-, S-chloromethyl-methane-, S-(2-chloroethyl)-methane-, S-(3-chloro-n-propyl)-methane-, S-methyl-ethane-, S-ethyl-ethane-, S-n-propyl-ethane-, S-iso-propyl-ethane-, S-n-butyl-ethane-, S-iso-butyl-ethane-, S-sec.-butyl-ethane-, S-tert.-butyl-ethane-, S-allyl-ethane-, S-propenyl-ethane-, S-but-2-enyl-ethane-, S-but-3-enyl-ethane-, S-propynyl-ethane-, S-but-1-ynyl-ethane-, S-chloromethyl-ethane-, S-(2-chloroethyl)-ethane-, S-(3-chloro-n-propyl)-ethane-, S-methyl-n-propane-, S-ethyl-n-propane-, S-n-propyl-n-propane-, S-iso-propyl-n-propane-, S-n-butyl-n-propane-, S-iso-butyl-n-propane-, S-sec.-butyl-n-propane-, S-tert.-butyl-n-propane-, S-allyl-n-propane-, S-propenyl-n-propane-, S-but-2-enyl-n-propane-, S-but-3-enyl-n-propane-, S-propynyl-n-propane-, S-but-1-ynyl-n-propane-, S-chloromethyl-n-propane-, S-(2-chloroethyl)-n-propane, S-(3-chloro-n-propyl)-n-propane-, S-methyl-iso-propane-, S-ethyl-iso-propane-, S-n-propyl-iso-propane-, S-iso-propyl-iso-propane-, S-n-butyl-iso-propane-, S-iso-butyl-iso-propane-, S-sec.-butyl-iso-propane-, S-tert.-butyl-iso-propane-, S-allyl-iso-propane-, S-propenyl-iso-propane-, S-but-2-enyl-iso-propane-, S-but-3-enyl-iso-propane-, S-propynyl-iso-propane-, S-but-1-ynyl-iso-propane-, S-chloromethyl-iso-propane-, S-(2-chloroethyl)-iso-propane-, S-(3-chloro-n-propyl)-iso-propane-, S-methyl-n-butane-, S-ethyl-n-butane-, S-n-propyl-n-butane-, S-iso-propyl-n-butane-, S-n-butyl-n-butane-, S-iso-butyl-n-butane-, S-sec.-butyl-n-butane-, S-tert.-butyl-n-butane-, S-allyl-n-butane-, S-propenyl-n-butane-, S-but-2-enyl-n-butane-, S-but-3-enyl-n-butane-, S-propynyl-n-butane-, S-but-1-ynyl-n-butane-, S-chloromethyl-n-butane-, S-(2-chloroethyl)-n-butane-, S-(3-chloro-n-propyl)-n-butane-, S-methyl-iso-butane-, S-ethyl-iso-butane-, S-n-propyl-iso-butane-, S-iso-propyl-iso-butane-, S-n-butyl-iso-butane-, S-iso-butyl-iso-butane-, S-sec.-butyl-iso-butane-, S-tert.-butyl-iso-butane-, S-allyl-iso-butane-, S-propenyl-iso-butane-, S-but-2-enyl-iso-butane-, S-but-3-enyl-iso-butane-, S-propynyl-iso-butane-, S-but-1-ynyl-iso-butane-, S-chloromethyl-iso-butane-, S-(2-chloroethyl)-iso-butane-, S-(3-chloro-n-propyl)-iso-butane-, S-methyl-sec.-butane-, S-ethyl-sec.-butane-, S-n-propyl-sec.-butane-, S-iso-propyl-sec.-butane-, S-n-butyl-sec.-butane-, S-iso-butyl-sec.-butane-, S-sec.-butyl-sec.-butane-, S-tert.-butyl-sec.-butane-, S-allyl-sec.-butane-, S-propenyl-sec.-butane-, S-but-2-enyl-sec.-butane-, S-but-3-enyl-sec.-butane-, S-propynyl-sec.-butane-, S-but-1-ynyl-sec.-butane-, S-chloromethyl-sec.-butane-, S-(2-chloroethyl)-sec.-butane-, S-(3-chloro-n-propyl)-sec.-butane-, S-methyl-tert.-butane-, S-ethyl-tert.-butane-, S-n-propyl-tert.-butane-, S-iso-propyl-tert.-butane-, S-n-butyl-tert.-butane-, S-iso-butyl-tert.-butane-, S-sec.-butyl-tert.-butane-, S-tert.-butyl-tert.-butane-, S-allyl-tert.-butane-, S-propenyl-tert.-butane-, S-but-2-enyl-tert.-butane-, S-but-3-enyl-tert.-butane-, S-propynyl-tert.-butane-, S- but-1-ynyl-tert.-butane-, S-chloromethyl-tert.-butane-, S-(2-chloroethyl)-tert.-butane- and S-(3-chloro-n-propyl)-tert.-butane-thionothiolphosphonic acid monoester chloride.

The phenols (III) also to be used as starting compounds are known. The following may be mentioned as specific examples thereof: phenol and 2-cyano-, 2-nitro-, 2-chloro-, 2-bromo-, 2-phenyl-, 2-methyl-, 2-ethyl-, 2-n-propyl-, 2-iso-propyl-, 2-n-butyl-, 2-iso-butyl-, 2-sec.-butyl-, 2-tert.-butyl-, 2-methoxy-, 2-ethoxy-, 2-n-propoxy-, 2-iso-propoxy-, 2-n-butoxy-, 2-iso-butoxy-, 2-sec.-butoxy-, 2-tert.-butoxy-, 2-methylthio-, 2-ethylthio-, 2-n-propylthio-, 2-iso-propylthio-, 2-carbomethoxy-, 2-carbethoxy-, 2-carbo-n-propoxy-, 2-carbo-iso-propoxy-, 3-chloro-, 3-methoxy-, 3-ethoxy-, 4-chloro-, 4-cyano-, 4-nitro-, 4-methylthio-, 4-ethylthio-, 4-methoxy-, 4-ethoxy-, 4-methylsulphonyl-, 4-ethylsulphonyl-, 4-methyl-, 4-ethyl-, 4-n-propyl-, 4-iso-propyl-, 4-n-butyl, 4-iso-butyl-, 4-sec.-butyl-, 4-tert.-butyl-, 2,4-dichloro- and 2,4-dimethylphenol.

O-Aryldithioalkanephosphonic acid monoesters (IV), and their salts, also to be used as starting compounds, have been described in the literature; they all can be obtained from the O-aryl-thionoalkanephosphonic acid monoester halides known from the literature, hydrogen sulphide and an alkali metal salt, for example potassium carbonate.

The following may be mentioned as specific examples thereof: O-phenyl-methane-, O-phenyl-ethane-, O-phenyl-n-propane-, O-phenyl-iso-propane-, O-phenyl-n-butane-, O-phenyl-iso-butane-, O-phenyl-sec.-butane-, O-phenyl-tert.-butane-, O-(2-cyano-phenyl)-methane-, O-(2-cyano-phenyl)-ethane-, O-(2-cyano-phenyl)-n-propane-, O-(2-cyano-phenyl)-iso-propane-, O-(2-cyano-phenyl)-n-butane-, O-(2-cyano-phenyl)-iso-butane-, O-(2-cyano-phenyl)-sec.-butane-, O-(2-cyano-phenyl)-tert.-butane-, O-(2-nitro-phenyl)-methane-, O-(2-nitro-phenyl)-ethane-, O-(2-nitro-phenyl)-n-propane-, O-(2-nitro-phenyl)-iso-propane-, O-(2-nitro-phenyl)-n-butane-, O-(2-nitro-phenyl)-iso-butane-, O-(2-nitro-phenyl)-sec.-butane-, O-(2-nitro-phenyl)-tert.-butane-, O-(2-chloro-phenyl)-methane-, O-(2-chloro-phenyl)-ethane-, O-(2-chloro-phenyl)-n-propane-, O-(2-chloro-phenyl)-iso-propane-, O-(2-chloro-phenyl)-n-butane-, O-(2-chloro-phenyl)-iso-butane-, O-(2-chloro-phenyl)-sec.-butane-, O-(2-chloro-phenyl)-tert.-butane-, O-(2-bromo-phenyl)-methane-, O-(2-bromo-phenyl)-ethane-, O-(2-bromo-phenyl)-n-propane-, O-(2-bromo-phenyl)-iso-propane-, O-(2-bromo-phenyl)-n-butane-, O-(2-bromo-phenyl)-iso-butane-, O-(2-bromo-phenyl)-sec.-butane-, O-(2-bromo-phenyl)-tert.-butane-, O-(2-phenyl-phenyl)-methane-, O-(2-phenyl-phenyl)-ethane-, O-(2-phenyl-phenyl)-n-propane-, O-(2-phenyl-phenyl)-iso-propane-, O-(2-phenyl-phenyl)-n-butane-, O-(2-phenyl-phenyl)-iso-butane-, O-(2-phenyl-phenyl)-sec.-butane-, O-(2-phenyl-phenyl)-tert.-butane-, O-(2-methyl-phenyl)-methane-, O-(2-methyl-phenyl)-ethane-, O-(2-methyl-phenyl)-n-propane-, O-(2-methyl-phenyl)-iso-propane-, O-(2-methyl-phenyl)-n-butane-, O-(2-methyl-phenyl)-iso-butane-, O-(2-methyl-phenyl)-sec.-butane-, O-(2-methyl-phenyl)-tert.-butane-, O-(2-ethyl-phenyl)-methane-, O-(2-ethyl-phenyl)-ethane-, O-(2-ethyl-phenyl)-n-propane-, O-(2-ethyl-phenyl)-iso-propane-, O-(2-ethyl-phenyl)-n-butane-, O-(2-ethyl-phenyl)-iso-butane-, O-(2-ethyl-phenyl)-sec.-butane-, O-(2-ethyl-phenyl)-tert.-butane-, O-(2-n-propyl-phenyl)-methane-, O-(2-n-propyl-phenyl)-ethane-, O-(2-n-propyl-phenyl)-n-propane-, O-(2-n-propyl-phenyl)-iso-propane-, O-(2-n-propyl-phenyl)-n-butane-, O-(2-n-propylphenyl)-iso-butane-, O-(2-n-propyl-phenyl)-sec.-butane-, O-(2-n-propyl-phenyl)-tert.-butane-, O-(2-iso-propyl-phenyl)-methane-, O-(2-iso-propyl-phenyl)-ethane-, O-(2-iso-propyl-phenyl)-n-propane-, O-(2-iso-propyl-phenyl)-iso-propane-, O-(2-iso-propyl-phenyl)-n-butane-, O-(2-iso-propyl-phenyl)-iso-butane-, O-(2-iso-propyl-phenyl)-sec.-butane-, O-(2-iso-propyl-phenyl)-tert.-butane-, O-(2-n-butyl-phenyl)-methane-, O-(2-n-butyl-phenyl)-ethane-, O-(2-n-butyl-phenyl)-n-propane-, O-(2-n-butyl-phenyl)-iso-propane-, O-(2-n-butyl-phenyl)-n-butane-, O-(2-n-butyl-phenyl)-iso-butane-, O-(2-n-butyl-phenyl)-sec.-butane-, O-(2-n-butyl-phenyl)-tert.-butane-, O-(2-iso-butyl-phenyl)-methane-, O-(2-iso-butyl-phenyl)-ethane-, O-(2-iso-butyl-phenyl)-n-propane, O-(2-iso-butyl-phenyl)-iso-propane-, O-(2-iso-butyl-phenyl)-n-butane-, O-(2-iso-butyl-phenyl)-iso-butane-, O-(2-iso-butyl-phenyl)-sec.-butane-, O-(2-iso-butyl-phenyl)-tert.-butane-, O-(2-sec.-butyl-phenyl)-methane-, O-(2-sec.-butyl-phenyl)-ethane-, O-(2-sec.-butyl-phenyl)-n-propane-, O-(2-sec.-butyl-phenyl)-iso-propane-, O-(2-sec.-butyl-phenyl)-n-butane-, O-(2-sec.-butyl-phenyl)-iso-butane-, O-(2-sec.-butyl-phenyl)-sec.-butane-, O-(2-sec.-butyl-phenyl)-tert.-butane-, O-(2-tert.-butyl-phenyl)-methane-, O-(2-tert.-butyl-phenyl)-ethane-, O-(2-tert.-butyl-phenyl)-n-propane-, O-(2-tert.-butyl-phenyl)-iso-propane-, O-(2-tert.-butyl-phenyl)-n-butane-, O-(2-tert.-butyl-phenyl)-iso-butane-, O-(2-tert.-butyl-phenyl)-sec.-butane-, O-(2-tert.-butyl-phenyl)-tert.-butane-, O-(2-methoxy-phenyl)-methane-, O-(2-methoxy-phenyl)-ethane-, O-(2-methoxy-phenyl)-n-propane-, O-(2-methoxy-phenyl)-iso-propane-, O-(2-methoxy-phenyl)-n-butane-, O-(2-methoxy-phenyl)-iso-butane-, O-(2-methoxy-phenyl)-sec.-butane-, O-(2-methoxy-phenyl)-tert.-butane-, O-(2-ethoxy-phenyl)-methane-, O-(2-ethoxy-phenyl)-ethane-, O-(2-ethoxy-phenyl)-n-propane-, O-(2-ethoxy-phenyl)-iso-propane-, O-(2-ethoxy-phenyl)-n-butane-, O-(2-ethoxy-phenyl)-iso-butane-, O-(2-ethoxy-phenyl)-sec.-butane-, O-(2-ethoxy-phenyl)-tert.-butane-, O-(2-n-propoxy-phenyl)-methane-, O-(2-n-propoxy-phenyl)-ethane-, O-(2-propoxy-phenyl)-n-propane-, O-(2-n-propoxy-phenyl)-iso-propane-, O-(2-n-propoxy-phenyl)-n-butane-, O-(2-n-propoxy-phenyl)-iso-butane-, O-(2-n-propoxy-phenyl)-sec.-butane-, O-(2-n-propoxy-phenyl)-tert.-butane-, O-(2-iso-propoxy-phenyl)-methane-, O-(2-iso-propoxy-phenyl)-ethane-, O-(2-iso-propoxy-phenyl)-n-propane-, O-(2-iso-propoxy-phenyl)-iso-propane-, O-(2-iso-propoxy-phenyl)-n-butane-, O-(2-iso-propoxy-phenyl)-iso-butane-, O-(2-iso-propoxy-phenyl)-sec.-butane-, O-(2-iso-propoxy-phenyl)-tert.-butane-, O-(2-n-butoxy-phenyl)-methane-, O-(2-n-butoxy-phenyl)-ethane-, O-(2-n-butoxy-phenyl)-n-propane-, O-(2-n-butoxy-phenyl)-iso-propane-, O-(2-n-butoxy-phenyl)-n-butane-, O-(2-n-butoxy-phenyl)-iso-butane-, O-(2-butoxy-phenyl)-sec.-butane-, O-(2-n-butoxy-phenyl)-tert.-butane-, O-(2-iso-butoxy-phenyl)-methane-, O-(2-iso-butoxy-phenyl)-ethane-, O-(2-iso-butoxy-phenyl)-n-propane-, O-(2-iso-butoxy-phenyl)-iso-propane-, O-(2-iso-butoxy-phenyl)-n-butane-, O-(2-iso-butoxy-phenyl)-iso-butane-, O-(2-iso-butoxy-phenyl)-sec.-butane-, O-(2-iso-butoxy-phenyl)-tert.-butane-, O-(2-sec.-butoxy-phenyl)-methane-, O-(2-sec.-butoxy-phenyl)-ethane-, O-(2-sec.-butoxy-phenyl)-n-propane-, O-(2-sec.-butoxy-phenyl)-iso-propane-, O-(2-sec.-butoxy-phenyl)-n-butane-, O-(2-sec.-butoxy-phenyl)-iso-butane-, O-(2-sec.-butoxy-phenyl)-sec.-butane-, O-(2-sec.-butoxy-phenyl)-tert.-butane-, O-(2- tert.-butoxy-phenyl)-methane-, O-(2-tert.-butoxy-phenyl)-ethane-, O-(2-tert.-butoxy-phenyl)-n-propane-, O-(2-tert.-butoxy-phenyl)-iso-propane-, O-(2-tert.-butoxy-phenyl)-n-butane-, O-(2-tert.-butoxy-phenyl)-iso-butane-, O-(2-tert.-butoxy-phenyl)-sec.-butane-, O-(2-tert.-butoxy-phenyl)-tert.-butane-, O-(2-methylthio-phenyl)-methane-, O-(2-methylthio-phenyl)-ethane-, O-(2-methylthio-phenyl)-n-propane-, O-(2-methylthio-phenyl)-iso-propane-, O-(2-methylthio-phenyl)-n-butane-, O-(2-methylthio-phenyl)-iso-butane-, O-(2-methylthio-phenyl)-sec.-butane-, O-(2-methylthio-phenyl)-tert.-butane-, O-(2-ethylthio-phenyl)-methane-, O-(2-ethylthio-phenyl)-ethane-, O-(2-ethylthio-phenyl)-n-propane-, O-(2-ethylthio-phenyl)-iso-propane-, O-(2-ethylthio-phenyl)-n-butane-, O-(2-ethylthio-phenyl)-iso-butane-, O-(2-ethylthio-phenyl)-sec.-butane-, O-(2-ethylthio-phenyl)-tert.-butane-, O-(2-n-propylthio-phenyl)-methane-, O-(2-n-propylthio-phenyl)-ethane-, O-(2-n-propylthio-phenyl)-n-propane-, O-(2-n-propylthio-phenyl)-iso-propane-, O-(2-n-propylthio-phenyl)-n-butane-, O-(2-n-propylthio-phenyl)-iso-butane-, O-(2-propylthio-phenyl)-sec.-butane-, O-(2-n-propylthio-phenyl)-tert.-butane-, O-(2-iso-propylthio-phenyl)-methane-, O-(2-iso-propylthio-phenyl)-ethane-, O-(2-iso-propylthio-phenyl)-n-propane-, O-(2-iso-propylthio-phenyl)-iso-propane-, O-(2-iso-propylthio-phenyl)-n-butane-, O-(2-iso-propylthio-phenyl)-iso-butane-, O-(2-iso-propylthio-phenyl)-sec.-butane-, O-(2-iso-propylthio-phenyl)-tert.-butane-, O-(2-carbomethoxy-phenyl)-methane-, O-(2-carbomethoxy-phenyl)-ethane-, O-(2-carbomethoxy-phenyl)-n-propane-, O-(2-carbomethoxy-phenyl)-iso-propane-, O-(2-carbomethoxy-phenyl)-n-butane-, O-(2-carbomethoxy-phenyl)-iso-butane-, O-(2-carbomethoxy-phenyl)-sec.-butane-, O-(2-carbomethoxy-phenyl)-tert.-butane-, O-(2-carbethoxy-phenyl)-methane-, O-(2-carbethoxy-phenyl)-ethane-, O-(2-carbethoxy-phenyl)-n-propane-, O-(2-carbethoxy-phenyl)-iso-propane-, O-(2-carbethoxy-phenyl)-n-butane-, O-(2-carbethoxy-phenyl)-iso-butane-, O-(2-carbethoxy-phenyl)-sec.-butane-, O-(2-carbethoxy-phenyl)-tert.-butane-, O-(2-carbo-n-propoxy-phenyl)-methane-, O-(2-carbo-n-propoxy-phenyl)-ethane-, O-(2-carbo-n-propoxy-phenyl)-n-propane-, O-(2-carbo-n-propoxy-phenyl)-iso-propane, O-(2-carbo-n-propoxy-phenyl)-n-butane-, O-(2-carbo-n-propoxy-phenyl)-sec.-butane-, O-(2-carbo-n-propoxy-phenyl)-iso-butane-, O-(2-carbo-n-propoxy-phenyl)-tert.-butane-, O-(2-carbo-iso-propoxy-phenyl)-methane-, O-(2-carbo-iso-propoxy-phenyl)-ethane-, O-(2-carbo-iso-propoxy-phenyl)-n-propane-, O-(2-carbo-iso-propoxy-phenyl)-iso-propane-, O-(2-carbo-iso-propoxy-phenyl)-n-butane-, O-(2-carbo-iso-propoxy-phenyl)-iso-butane-, O-(2-carbo-iso-propoxy-phenyl)-sec.-butane-, O-(2-carbo-iso-propoxy-phenyl)-tert.-butane-, O-(3-chloro-phenyl)-methane-, O-(3-chloro-phenyl)-ethane-, O-(3-chloro-phenyl)-n-propane-, O-(3-chloro-phenyl)-iso-propane-, O-(3-chloro-phenyl)-n-butane-, O-(3-chloro-phenyl)-iso-butane-, O-(3-chloro-phenyl)-sec.-butane-, O-(3-chloro-phenyl)-tert.-butane-, O-(3-methoxy-phenyl)-methane-, O-(3-methoxy-phenyl)-ethane-, O-(3-methoxy-phenyl)-n-propane-, O-(3-methoxy-phenyl)-iso-propane-, O-(3-methoxy-phenyl)-n-butane-, O-(3-methoxy-phenyl)-iso-butane-, O-(3-methoxy-phenyl)-sec.-butane-, O-(3-methoxy-phenyl)-tert.-butane-, O-(3-ethoxy-phenyl)-methane-, O-(3-ethoxy-phenyl)-ethane-, O-(3-ethoxy-phenyl)-n-propane-, O-(3-ethoxy-phenyl)-iso-propane-, O-(3-ethoxy-phenyl)-n-butane-, O-(3-ethoxy-phenyl)-iso-butane, O-(3-ethoxy-phenyl)-sec.-butane-, O-(3-ethoxy-phenyl)-tert.-butane-, O-(4-chloro-phenyl)-methane-, O-(4-chloro-phenyl)-ethane-, O-(4-chloro-phenyl)-n-propane-, O-(4-chloro-phenyl)-iso-propane-, O-(4-chloro-phenyl)-n-butane-, O-(4-chloro-phenyl)-iso-butane-, O-(4-chloro-phenyl)-sec.-butane-, O-(4-chloro-phenyl)-tert.-butane-, O-(4-cyano-phenyl)-methane-, O-(4-cyano-phenyl)-ethane-, O-(4-cyano-phenyl)-n-propane, O-(4-cyano-phenyl)-iso-propane-, O-(4-cyano-phenyl)-n-butane-, O-(4-cyano-phenyl)-iso-butane-, O-(4-cyano-phenyl)-sec.-butane-, O-(4-cyano-phenyl)-tert.-butane-, O-(4-nitro-phenyl)-methane-, O-(4-nitro-phenyl)-ethane-, O-(4-nitro-phenyl)-n-propane-, O-(4-nitro-phenyl)-iso-propane-, O-(4-nitro-phenyl)-n-butane-, O-(4-nitro-phenyl)-iso-butane-, O-(4-nitro-phenyl)-sec.-butane-, O-(4-nitro-phenyl)-tert.-butane-, O-(4-methylthio-phenyl)-methane-, O-(4-methylthio-phenyl)-ethane-, O-(4-methylthio-phenyl)-n-propane-, O-(4-methylthio-phenyl)-iso-propane-, O-(4-methylthio-phenyl)-n-butane-, O-(4-methylthio-phenyl)-iso-butane-, O-(4-methylthio-phenyl)-sec.-butane-, O-(4-methylthio-phenyl)-tert.-butane-, O-(4-ethylthio-phenyl)-methane-, O-(4-ethylthio-phenyl)-ethane-, O-(4-ethylthio-phenyl)-n-propane, O-(4-ethylthio-phenyl)-iso-propane, O-(4-ethylthio-phenyl)-n-butane-, O-(4-ethylthio-phenyl)-iso-butane-, O-(4-ethylthio-phenyl)-sec.-butane-, O-(4-ethylthio-phenyl)-tert.-butane-, O-(4-methoxy-phenyl)-methane-, O-(4-methoxy-phenyl)-ethane-, O-(4-methoxy-phenyl)-n-propane-, O-(4-methoxy-phenyl)-iso-propane-, O-(4-methoxy-phenyl)-n-butane-, O-(4-methoxy-phenyl)-iso-butane-, O-(4-methoxy-phenyl)-sec.-butane-, O-(4-methoxy-phenyl)-tert.-butane-, O-(4-ethoxy-phenyl)-methane-, O-(4-ethoxy-phenyl)-ethane-, O-(4-ethoxy-phenyl)-n-propane-, O-(4-ethoxy-phenyl)-iso-propane-, O-(4-ethoxy-phenyl)-n-butane-, O-(4-ethoxy-phenyl)-iso-butane-, O-(4-ethoxy-phenyl)-sec.-butane-, O-(4-ethoxy-phenyl)-tert.-butane-, O-(4-methylsulphonyl-phenyl)-methane-, O-(4-methylsulphonyl-phenyl)-ethane-, O-(4-methylsulphonyl-phenyl)-n-propane-, O-(4-methylsulphonyl-phenyl)-iso-propane-, O-(4-methylsulphonyl-phenyl)-n-butane-, O-(4-methylsulphonyl-phenyl)-iso-butane-, O-(4-methylsulphonyl-phenyl)-sec.-butane-, (O-(4-methylsulphonyl-phenyl)-tert.-butane-, O-(4-ethylsulphonyl-phenyl)-methane-, O-(4-ethylsulphonyl-phenyl)-ethane-, O-(4-ethylsulphonyl-phenyl)-n-propane-, O-(4-ethylsulphonyl-phenyl)-iso-propane-, O-(4-ethylsulphonyl-phenyl)-n-butane-, O-(4-ethylsulphonyl-phenyl)-iso-butane-, O-(4-ethylsulphonyl-phenyl)-sec.-butane-, O-(4-ethylsulphonyl-phenyl)-tert.-butane-, O-(4-methyl-phenyl)-methane-, O-(4-methyl-phenyl)-ethane-, O-(4-methyl-phenyl)-n-propane, O-(4-methyl-phenyl)-iso-propane-, O-(4-methyl-phenyl)-n-butane-, O-(4-methyl-phenyl)-iso-butane-, O-(4-methyl-phenyl)-sec.-butane-, O-(4-methyl-phenyl)-tert.-butane-, O-(4-ethyl-phenyl)-methane-, O-(4-ethyl-phenyl)-ethane-, O-(4-ethyl-phenyl)-n-propane-, O-(4-ethyl-phenyl)-iso-propane-, O-(4-ethyl-phenyl)-n-butane-, O-(4-ethyl-phenyl)-iso-butane-, O-(4-ethyl-phenyl)-sec.-butane-, O-(4-ethyl-phenyl)-tert.-butane-, O-(4-n-propyl-phenyl)-methane-, O-(4-n-propyl-phenyl)-ethane-, O-( 4-n-propyl-phenyl)-n-propane-, O-(4-n-propyl-phenyl)-iso-propane-, O-(4-n-propyl-phenyl)-n-butane-, O-(4-n-propyl-phenyl)-iso-butane-, O-(4-n-propyl-phenyl)-sec.-butane-, O-(4-n-propyl-phenyl)-tert.-butane-, O-(4-iso-propyl-phenyl)-methane-, O-(4-iso-propyl-phenyl)-ethane-, O-(4-iso-propyl-phenyl)-n-propane-, O-(4-iso-propyl-phenyl)-iso-propane-, O-(4-iso-propyl-phenyl)-n-butane-, O-(4- iso-propyl-phenyl)-iso-butane-, O-(4-iso-propyl-phenyl)-sec.-butane-, O-(4-iso-propyl-phenyl)-tert.-butane-, O-(4-n-butyl-phenyl)-methane-, O-(4-n-butyl-phenyl)-ethane-, O-(4-n-butyl-phenyl)-n-propane-, O-(4-n-butyl-phenyl)-iso-propane-, O-(4-n-butyl-phenyl)-n-butane-, O-(4-n-butyl-phenyl)-iso-butane-, O-(4-n-butyl-phenyl)-sec.-butane-, O-(4-n-butyl-phenyl)-tert.-butane-, O-(4-iso-butyl-phenyl)-methane-, O-(4-iso-butyl-phenyl)-ethane-, O-(4-iso-butyl-phenyl)-n-propane-, O-(4-iso-butyl-phenyl)-iso-propane-, O-(4-iso-butyl-phenyl)-n-butane-, O-(4-iso-butyl-phenyl)-iso-butane-, O-(4-iso-butyl-phenyl)-sec.-butane-, O-(4-iso-butyl-phenyl)-tert.-butane-, O-(4-sec.-butyl-phenyl)-methane-, O-(4-sec.-butyl-phenyl)-ethane-, O-(4-sec.-butyl-phenyl)-n-propane-, O-(4-sec.-butyl-phenyl)-iso-propane-, O-(4-sec.-butyl-phenyl)-n-butane-, O-(4-sec.-butyl-phenyl)-iso-butane-, O-(4-sec.-butyl-phenyl)-sec.-butane-, O-(4-sec.-butyl-phenyl)-tert.-butane-, O-(4-tert.-butyl-phenyl)-methane-, O-(4-tert.-butyl-phenyl)-ethane-, O-(4-tert.-butyl-phenyl)-n-propane-, O-(4-tert.-butyl-phenyl)-iso-propane-, O-(4-tert.-butyl-phenyl)-n-butane-, O-(4-tert.-butyl-phenyl)-iso-butane-, O-(4-tert.-butyl-phenyl)-sec.-butane-, O-(4-tert.-butyl-phenyl)-tert.-butane-, O-(2,4-dichloro-phenyl)-methane-, O-(2,4-dichloro-phenyl)-ethane-, O-(2,4-dichloro-phenyl)-n-propane-, O-(2,4-dichloro-phenyl)-iso-propane, O-(2,4-dichloro-phenyl)-n-butane-, O-(2,4-dichloro-phenyl)-iso-butane-, O-(2,4-dichloro-phenyl)-sec.-butane-, O-(2,4-dichloro-phenyl)-tert.-butane-, O-(2,4-dimethyl-phenyl)-methane-, O-(2,4-dimethyl-phenyl)-ethane-, O-(2,4-dimethyl-phenyl)-n-propane-, O-(2,4-dimethyl-phenyl)-iso-propane-, O-(2,4-dimethyl-phenyl)-n-butane-, O-(2,4-dimethyl-phenyl)-iso-butane-, O-(2,4-dimethyl-phenyl)-sec.-butane- and O-(2,4-dimethyl-phenyl)-tert.-butane-dithiophosphonic acid monoester and the corresponding alkali metal salts and alkaline earth metal salts.

The halides (V) required as starting materials are known and can readily be prepared in accordance with known methods. The following may be mentioned as specific examples thereof: methyl-, ethyl-, n-propyl-, iso-propyl-, n-butyl-, iso-butyl-, tert.-butyl-, allyl-, propenyl-, but-2-enyl-, but-3-enyl, propynyl-, but-1-ynyl-, chloromethyl-, 2-chloroethyl-, 3-chloro-n-propyl- and 4-chloro-n-butyl chloride or bromide.

Furthermore, O-arylthionoalkanephosphonic acid monoester halides (VI) also used as starting materials are known; they all can be prepared in accordance with processes known from the literature (see, for example, Newallis et al., J. Chem. Eng. Data 15 (1970) 3, 455–457; Grapov et al., Zh. Obsk. Khim. 44 (106) 1974, 3, 533–538).

The following may be mentioned as specific examples thereof: O-phenyl-methane-, O-phenyl-ethane-, O-phenyl-n-propane-, O-phenyl-iso-propane-, O-phenyl-n-butane-, O-phenyl-iso-butane-, O-phenyl-sec.-butane-, O-phenyl-tert.-butane-, O-(2-cyano-phenyl)-methane-, O-(2-cyano-phenyl)-ethane-, O-(2-cyano-phenyl)-n-propane-, O-(2-cyano-phenyl)-iso-propane-, O-(2-cyano-phenyl)-n-butane-, O-(2-cyano-phenyl)-iso-butane-, O-(2-cyano-phenyl)-sec.-butane-, O-(2-cyano-phenyl)-tert.-butane-, O-(2-nitro-phenyl)-methane-, O-(2-nitro-phenyl)-ethane-, O-(2-nitro-phenyl)-n-propane-, O-(2-nitro-phenyl)-iso-propane, O-(2-nitro-phenyl)-n-butane-, O-(2-nitro-phenyl)-iso-butane-, O-(2-nitro-phenyl)-sec.-butane-, O-(2-nitro-phenyl)-tert.-butane-, O-(2-chloro-phenyl)-methane-, O-(2-chloro-phenyl)-ethane-, O-(2-chloro-phenyl)-n-propane-, O-(2-chloro-phenyl)-iso-propane, O-(2-chloro-phenyl)-n-butane, O-(2-chloro-phenyl)-iso-butane-, O-(2-chloro-phenyl)-sec.-butane-, O-(2-chloro-phenyl)-tert.-butane-, O-(2-bromo-phenyl)-methane-, O-(2-bromo-phenyl)-ethane-, O-(2-bromo-phenyl)-n-propane-, O-(2-bromo-phenyl)-iso-propane-, O-(2-bromo-phenyl)-n-butane-, O-(2-bromo-phenyl)-iso-butane-, O-(2-bromo-phenyl)-sec.-butane-, O-(2-bromo-phenyl)-tert.-butane-, O-(2-phenyl-phenyl)-methane-, O-(2-phenyl-phenyl)-ethane-, O-(2-phenyl-phenyl)-n-propane-, O-(2-phenyl-phenyl)-iso-propane-, O-(2-phenyl-phenyl)-n-butane-, O-(2-phenyl-phenyl)-iso-butane-, O-(2-phenyl-phenyl)-sec.-butane-, O-(2-phenyl-phenyl)-tert.-butane-, O-(2-methyl-phenyl)-methane-, O-(2-methyl-phenyl)-ethane-, O-(2-methyl-phenyl)-n-propane-, O-(2-methyl-phenyl)-iso-propane-, O-(2-methylphenyl)-n-butane-, O-(2-methyl-phenyl)-iso-butane-, O-(2-methyl-phenyl)-sec.-butane-, O-(2-methyl-phenyl)-tert.-butane-, O-(2-ethyl-phenyl)-methane-, O-(2-ethyl-phenyl)-ethane-, O-(2-ethyl-phenyl)-n-propane-, O-(2-ethyl-phenyl)-iso-propane-, O-(2-ethyl-phenyl)-n-butane-, O-(2-ethyl-phenyl)-iso-butane-, O-(2-ethyl-phenyl)-sec.-butane-, O-(2-ethyl-phenyl)-tert.-butane-, O-(2-n-propyl-phenyl)-methane-, O-(2-n-propyl-phenyl)-ethane-, O-(2-n-propyl-phenyl)-n-propane-, O-(2-n-propyl-phenyl)-iso-propane-, O-(2-n-propyl-phenyl)-n-butane-, O-(2-n-propyl-phenyl)-iso-butane-, O-(2-n-propyl-phenyl)-sec.-butane-, O-(2-n-propyl-phenyl)-tert.-butane-, O-(2-iso-propyl-phenyl)-methane-, O-(2-iso-propyl-phenyl)-ethane-, O-(2-iso-propyl-phenyl)-n-propane-, O-(2-iso-propyl-phenyl)-iso-propane-, O-(2-iso-propyl-phenyl)-n-butane-, O-(2-iso-propyl-phenyl)-iso-butane, O-(2-iso-propyl-phenyl)-sec.-butane-, O-(2-iso-propyl-phenyl)-tert.-butane-, O-(2-n-butyl-phenyl)-methane-, O-(2-n-butyl-phenyl)-ethane-, O-(2-n-butyl-phenyl)-n-propane-, O-(2-n-butyl-phenyl)-iso-propane-, O-(2-n-butyl-phenyl)-n-butane-, O-(2-n-butyl-phenyl)-iso-butane-, O-(2-n-butyl-phenyl)-sec.-butane-, O-(2-n-butyl-phenyl)-tert.-butane-, O-(2-iso-butyl-phenyl)-methane-, O-(2-iso-butyl-phenyl)-ethane-, O-(2-iso-butyl-phenyl)-n-propane-, O-(2-iso-butyl-phenyl)-iso-propane-, O-(2-iso-butyl-phenyl)-n-butane-, O-(2-iso-butyl-phenyl)-iso-butane-, O-(2-iso-butyl-phenyl)-sec.-butane-, O-(2-iso-butyl-phenyl)-tert.-butane-, O-(2-sec.-butyl-phenyl)-methane-, O-(2-sec.-butyl-phenyl)-ethane-, O-(2-sec.-butyl-phenyl)-n-propane-, O-(2-sec.-butyl-phenyl)-iso-propane, O-(2-sec.-butyl-phenyl)-n-butane-, O-(2-sec.-butyl-phenyl)-iso-butane-, O-(2-sec.-butyl-phenyl)-sec.-butane-, O-(2-sec.-butyl-phenyl)-tert.-butane-, O-(2-tert.-butyl-phenyl)-methane-, O-(2-tert.-butyl-phenyl)-ethane-, O-(2-tert.-butyl-phenyl)-n-propane-, O-(2-tert.-butyl-phenyl)-iso-propane-, O-(2-tert.-butyl-phenyl)-n-butane-, O-(2-tert.-butyl-phenyl)-iso-butane-, O-(2-tert.-butyl-phenyl)-sec.-butane-, O-(2-tert.-butyl-phenyl)-tert.-butane-, O-(2-methoxy-phenyl)-methane-, O-(2-methoxy-phenyl)-ethane-, O-(2-methoxy-phenyl)-n-propane-, O-(2-methoxy-phenyl)-iso-propane-, O-(2-methoxy-phenyl)-n-butane-, O-(2-methoxy-phenyl)-iso-butane-, O-(2-methoxy-phenyl)-sec.-butane-, O-(2-methoxy-phenyl)-tert.-butane-, O-(2-ethoxy-phenyl)-methane-, O-(2-ethoxy-phenyl)-ethane-, O-(2-ethoxy-phenyl)-n-propane-, O-(2-ethoxy-phenyl)-iso-propane-, O-(2-ethoxy-phenyl)-n-butane-, O-(2-ethoxy-phenyl)-iso-butane-, O-(2-ethoxy-phenyl)-sec.-butane-, O-(2-ethoxy-phenyl)-tert.-butane-, O-(2-n-propoxy-phenyl)-methane-, O-(2-n-propoxy-phenyl)-ethane-, O-(2-n-propoxy-phenyl)-n-propane-, O-(2-n-propoxy-phenyl)-iso-propane-, O-(2-n-propoxy-phenyl)-n-butane-, O-(2-n-propoxy-phenyl)- iso-butane-, O-(2-n-propoxy-phenyl)-sec.-butane-, O-(2-n-propoxy-phenyl)-tert.-butane-, O-(2-iso-propoxy-phenyl)-methane-, O-(2-iso-propoxy-phenyl)-ethane-, O-(2-iso-propoxy-phenyl)-n-propane-, O-(2-iso-propoxy-phenyl)-iso-propane-, O-(2-iso-propoxy-phenyl)-n-butane-, O-(2-iso-propoxy-phenyl)-iso-butane-, O-(2-iso-propoxy-phenyl)-sec.-butane-, O-(2-iso-propoxy-phenyl)-tert.-butane-, O-(2-n-butoxy-phenyl)-methane-, O-(2-n-butoxy-phenyl)-ethane-, O-(2-n-butoxy-phenyl)-n-propane-, O-(2-n-butoxy-phenyl)-iso-propane-, O-(2-n-butoxy-phenyl)-n-butane-, O-(2-n-butoxy-phenyl)-iso-butane-, O-(2-n-butoxy-phenyl)-sec.-butane-, O-(2-n-butoxy-phenyl)-tert.-butane-, O-(2-iso-butoxy-phenyl)-methane-, O-(2-iso-butoxy-phenyl)-ethane-, O-(2-iso-butoxy-phenyl)-n-propane-, O-(2-iso-butoxy-phenyl)-iso-propane-, O-(2-iso-butoxy-phenyl)-n-butane-, O-(2-iso-butoxy-phenyl)-iso-butane-, O-(2-iso-butoxy-phenyl)-sec.-butane-, O-(2-iso-butoxy-phenyl)-tert.-butane-, O-(2-sec.-butoxy-phenyl)-methane-, O-(2-sec.-butoxy-phenyl)-ethane-, O-(2-sec.-butoxy-phenyl)-n-propane-, O-(2-sec.-butoxy-phenyl)-iso-propane-, O-(2-sec.-butoxy-phenyl)-n-butane-, O-(2-sec.-butoxy-phenyl)-iso-butane-, O-(2-sec.-butoxy-phenyl)-sec.-butane-, O-(2-sec.-butoxy-phenyl)-tert.-butane-, O-(2-tert.-butoxy-phenyl)-methane-, O-(2-tert.-butoxy-phenyl)-ethane-, O-(2-tert.-butoxy-phenyl)-n-propane-, O-(2-tert.-butoxy-phenyl)-iso-propane-, O-(2-tert.-butoxy-phenyl)-n-butane-, O-(2-tert.-butoxy-phenyl)-iso-butane-, O-(2-tert.-butoxy-phenyl)-sec.-butane-, O-(2-tert.-butoxy-phenyl)-tert.-butane-, O-(2-methylthio-phenyl)-methane-, O-(2-methylthio-phenyl)-ethane-, O-(2-methylthio-phenyl)-n-propane-, O-(2-methylthio-phenyl)-iso-propane-, O-(2-methylthio-phenyl)-n-butane-, O-(2-methylthio-phenyl)-iso-butane-, O-(2-methylthio-phenyl)-sec.-butane-, O-(2-methylthio-phenyl)-tert.-butane-, O-(2-ethylthio-phenyl)-methane-, O-(2-ethylthio-phenyl)-ethane-, O-(2-ethylthio-phenyl)-n-propane-, O-(2-ethylthio-phenyl)-iso-propane-, O-(2-ethylthio-phenyl)-n-butane-, O-(2-ethylthio-phenyl)-iso-butane-, O-(2-ethylthio-phenyl)-sec.-butane-, O-(2-ethylthio-phenyl)-tert.-butane-, O-(2-n-propylthio-phenyl)-methane-, O-(2-n-propylthio-phenyl)-ethane-, O-(2-n-propylthio-phenyl)-n-propane-, O-(2-n-propylthio-phenyl)-iso-propane-, O-(2-n-propylthio-phenyl)-n-butane-, O-(2-n-propylthio-phenyl)-iso-butane-, O-(2-n-propylthio-phenyl)-sec.-butane-, O-(2-n-propylthio-phenyl)-tert.-butane-, O-(2-iso-propylthio-phenyl)-methane-, O-(2-iso-propylthio-phenyl)-ethane-, O-(2-iso-propylthio-phenyl)-n-propane-, O-(2-iso-propylthio-phenyl)-iso-propane-, O-(2-iso-propylthio-phenyl)-n-butane-, O-(2-iso-propylthio-phenyl)-iso-butane-, O-(2-iso-propylthio-phenyl)-sec.-butane-, O-(2-iso-propylthio-phenyl)-tert.-butane-, O-(2-carbomethoxy-phenyl)-methane-, O-(2-carbomethoxy-phenyl)-ethane-, O-(2-carbomethoxy-phenyl)-n-propane-, O-(2-carbomethoxy-phenyl)-iso-propane-, O-(2-carbomethoxy-phenyl)-n-butane-, O-(2-carbomethoxy-phenyl)-iso-butane-, O-(2-carbomethoxy-phenyl)-sec.-butane-, O-(2-carbomethoxy-phenyl)-tert.-butane-, O-(2-carbethoxy-phenyl)-methane-, O-(2-carbethoxy-phenyl)-ethane-, O-(2-carbethoxy-phenyl)-n-propane-, O-(2-carbethoxy-phenyl)-iso-propane-, O-(2-carbethoxy-phenyl)-n-butane-, O-(2-carbethoxy-phenyl)-iso-butane-, O-(2-carbethoxy-phenyl)-sec.-butane-, O-(2-carbethoxy-phenyl)-tert.-butane-, O-(2-carbo-n-propoxy-phenyl)-methane-, O-(2-carbo-n-propoxy-phenyl)-ethane-, O-(2-carbo-n-propoxy-phenyl)-n-propane-, O-(2-carbo-n-propoxy-phenyl)-iso-propane-, O-(2-carbo-n-propoxy-phenyl)-n-butane-, O-(2-carbo-n-propoxy-phenyl)-sec.-butane-, O-(2-carbo-n-propoxy-phenyl)-iso-butane-, O-(2-carbo-n-propoxy-phenyl)-tert.-butane-, O-(2-carbo-iso-propoxy-phenyl)-methane-, O-(2-carbo-iso-propoxy-phenyl)-ethane-, O-(2-carbo-iso-propoxy-phenyl)-n-propane-, O-(2-carbo-iso-propoxy-phenyl)-iso-propane-, O-(2-carbo-iso-propoxy-phenyl)-n-butane-, O-(2-carbo-iso-propoxy-phenyl)-iso-butane-, O-(2-carbo-iso-propoxy-phenyl)-sec.-butane-, O-(2-carbo-iso-propoxy-phenyl)-tert.-butane-, O-(3-chloro-phenyl)-methane-, O-(3-chloro-phenyl)-ethane-, O-(3-chloro-phenyl)-n-propane-, O-(3-chloro-phenyl)-iso-propane-, O-(3-chloro-phenyl)-n-butane-, O-(3-chloro-phenyl)-iso-butane-, O-(3-chloro-phenyl)-sec.-butane-, O-(3-chloro-phenyl)-tert.-butane-, O-(3-methoxy-phenyl)-methane-, O-(3-methoxy-phenyl)-ethane-, O-(3-methoxy-phenyl)-n-propane-, O-(3-methoxy-phenyl)-iso-propane-, O-(3-methoxy-phenyl)-n-butane-, O-(3-methoxy-phenyl)-iso-butane-, O-(3-methoxy-phenyl)-sec.-butane-, O-(3-methoxy-phenyl)-tert.-butane-, O-(3-ethoxy-phenyl)-methane-, O-(3-ethoxy-phenyl)-ethane-, O-(3-ethoxy-phenyl)-n-propane, O-(3-ethoxy-phenyl)-iso-propane-, O-(3-ethoxy-phenyl)-n-butane-, O-(3-ethoxy-phenyl)-iso-butane-, O-(3-ethoxy-phenyl)-sec.-butane-, O-(3-ethoxy-phenyl)-tert.-butane-, O-(4-chloro-phenyl)-methane-, O-(4-chloro-phenyl)-ethane-, O-(4-chloro-phenyl)-n-propane-, O-(4-chloro-phenyl)-iso-propane-, O-(4-chloro-phenyl)-n-butane-, O-(4-chloro-phenyl)-iso-butane-, O-(4-chloro-phenyl)-sec.-butane-, O-(4-chloro-phenyl)-tert.-butane-, O-(4-cyano-phenyl)-methane-, O-(4-cyano-phenyl)-ethane-, O-(4-cyano-phenyl)-n-propane-, O-(4-cyano-phenyl)-iso-propane-, O-(4-cyano-phenyl)-n-butane-, O-(4-cyano-phenyl)-iso-butane-, O-(4-cyano-phenyl)-sec.-butane-, O-(4-cyano-phenyl)-tert.-butane-, O-(4-nitro-phenyl)-methane-, O-(4-nitro-phenyl)-ethane-, O-(4-nitro-phenyl)-n-propane-, O-(4-nitro-phenyl)-iso-propane-, O-(4-nitro-phenyl)-n-butane-, O-(4-nitro-phenyl)-iso-butane-, O-(4-nitro-phenyl)-sec.-butane-, O-(4-nitro-phenyl)-tert.-butane-, O-(4-methylthio-phenyl)-methane-, O-(4-methylthio-phenyl)-ethane-, O-(4-methylthio-phenyl)-n-propane-, O-(4-methylthio-phenyl)-iso-propane-, O-(4-methylthio-phenyl)-n-butane-, O-(4-methylthio-phenyl)-iso-butane-, O-(4-methylthio-phenyl)-sec.-butane-, O-(4-methylthio-phenyl)-tert.-butane-, O-(4-ethylthio-phenyl)-methane-, O-(4-ethylthio-phenyl)-ethane-, O-(4-ethylthio-phenyl)-n-propane-, O-(4-ethylthio-phenyl)-iso-propane-, O-(4-ethylthio-phenyl)-n-butane-, O-(4-ethylthio-phenyl)-iso-butane-, O-(4-ethylthio-phenyl)-sec.-butane-, O-(4-ethylthio-phenyl)-tert.-butane-, O-(4-methoxy-phenyl)-methane-, O-(4-methoxy-phenyl)-ethane-, O-(4-methoxy-phenyl)-n-propane-, O-(4-methoxy-phenyl)-iso-propane-, O-(4-methoxy)-n-butane-, O-(4-methoxy-phenyl)-iso-butane-, O-(4-methoxy-phenyl)-sec.-butane-, O-(4-methoxy-phenyl)-tert.-butane-, O-(4-ethoxy-phenyl)-methane-, O-(4-ethoxy-phenyl)-ethane-, O-(4-ethoxy-phenyl)-n-propane-, O-(4-ethoxy-phenyl)-iso-propane-, O-(4-ethoxy-phenyl)-n-butane-, O-(4-ethoxy-phenyl)-iso-butane-, O-(4-ethoxy-phenyl)-sec.-butane-, O-(4ethoxy-phenyl)-tert.-butane-, O-(4-methylsulphonyl-phenyl)-methane-, O-(4-methylsulphonyl-phenyl)-ethane-, O-(4-methylsulphonyl-phenyl)-n-propane-, O-(4-methylsulphonyl-phenyl)-iso-propane-, O-(4-methylsulphonyl-phenyl)-n-butane-, O-(4-methylsulphonyl-phenyl)-iso-butane-, O-(4-methylsulphonyl-phenyl)-sec.-butane-, O-(4-methylsulphonyl-phenyl)-tert.-butane-, O-(4- ethylsulphonyl-phenyl)-methane-, O-(4-ethylsulphonyl-phenyl)-ethane-, O-(4-ethylsulphonyl-phenyl)-n-propane-, O-(4-ethylsulphonyl-phenyl)-iso-propane-, O-(4-ethylsulphonyl-phenyl)-n-butane-, O-(4-ethylsulphonyl-phenyl)-iso-butane-, O-(4-ethylsulphonyl-phenyl)-sec.-butane-, O-(4-ethylsulphonyl-phenyl)-tert.-butane-, O-(4-methyl-phenyl)-methane-, O-(4-methyl-phenyl)-ethane-, O-(4-methyl-phenyl)-n-propane-, O-(4-methyl-phenyl)-iso-propane-, O-(4-methyl-phenyl)-n-butane-, O-(4-methyl-phenyl)-iso-butane-, O-(4-methyl-phenyl)-sec.-butane-, O-(4-methyl-phenyl)-tert.-butane-, O-(4-ethyl-phenyl)-methane-, O-(4-ethyl-phenyl)-ethane-, O-(4-ethyl-phenyl)-n-propane-, O-(4-ethyl-phenyl)-iso-propane-, O-(4-ethyl-phenyl)-n-butane-, O-(4-ethyl-phenyl)-iso-butane-, O-(4-ethyl-phenyl)-sec.-butane-, O-(4-ethyl-phenyl)-tert.-butane-, O-(4-n-propyl-phenyl)-methane-, O-(4-n-propyl-phenyl)-ethane-, O-(4-n-propyl-phenyl)-n-propane-, O-(4-n-propane-phenyl)-iso-propane-, O-(4-n-propyl-phenyl)-n-butane-, O-(4-n-propyl-phenyl)-iso-butane-, O-(4-n-propyl-phenyl)-sec.-butane-, O-(4-n-propylphenyl)-tert.-butane-, O-(4-iso-propyl-phenyl)-methane-, O-(4-iso-propyl-phenyl)-ethane-, O-(4-iso-propyl-phenyl)-n-propane-, O-(4-iso-propyl-phenyl)-iso-propane-, O-(4-iso-propyl-phenyl)-n-butane-, O-(4-iso-propyl-phenyl)-iso-butane-, O-(4-iso-propyl-phenyl)-sec.-butane-, O-(4-iso-propyl-phenyl)-tert.-butane-, O-(4-n-butyl-phenyl)-methane-, O-(4-n-butyl-phenyl)-ethane-, O-(4-n-butyl-phenyl)-n-propane-, O-(4-n-butyl-phenyl)-iso-propane-, O-(4-n-butyl-phenyl)-n-butane-, O-(4-n-butyl-phenyl)-iso-butane-, O-(4-n-butyl-phenyl)-sec.-butane-, O-(4-n-butyl-phenyl)-tert.-butane-, O-(4-iso-butyl-phenyl)-methane-, O-(4-iso-butyl-phenyl)-ethane-, O-(4-iso-butyl-phenyl)-n-propane-, O-(4-iso-butyl-phenyl)-iso-propane-, O-(4-iso-butyl-phenyl)-n-butane-, O-(4-iso-butyl-phenyl)-iso-butane-, O-(4-iso-butyl-phenyl)-sec.-butane-, O-(4-iso-butyl-phenyl)-tert.-butane-, O-(4-sec.-butyl-phenyl)-methane-, O-(4-sec.-butyl-phenyl)-ethane-, O-(4-sec.-butyl-phenyl)-n-propane-, O-(4-sec.-butyl-phenyl)-iso-propane-, O-(4-sec.-butyl-phenyl)-n-butane-, O-(4-sec.-butyl-phenyl)-iso-butane-, O-(4-sec.-butyl-phenyl)-sec.-butane-, O-(4-sec.-butyl-phenyl)-tert.-butane-, O-(4-tert.-butyl-phenyl)-methane-, O-(4-tert.-butyl-phenyl)-ethane-, O-(4-tert.-butyl-phenyl)-n-propane-, O-(4-tert.-butyl-phenyl)-iso-propane-, O-(4-tert.-butyl-phenyl)-n-butane-, O-(4-tert.-butyl-phenyl)-iso-butane-, O-(4-tert.-butyl-phenyl)-sec.-butane-, O-(4-tert.-butyl-phenyl)-tert.-butane-, O-(2,4-dichloro-phenyl)-methane-, O-(2,4-dichloro-phenyl)-ethane-, O-(2,4-dichloro-phenyl)-n-propane-, O-(2,4-dichloro-phenyl)-iso-propane-, O-(2,4-dichloro-phenyl)-n-butane-, O-(2,4-dichloro-phenyl)-iso-butane-, O-(2,4-dichloro-phenyl)-sec.-butane-, O-(2,4-dichloro-phenyl)-tert.-butane-, O-(2,4-dimethyl-phenyl)-methane-, O-(2,4-dimethyl-phenyl)-ethane-, O-(2,4-dimethyl-phenyl)-n-propane-, O-(2,4-dimethyl-phenyl)-iso-propane-, O-(2,4-dimethyl-phenyl)-n-butane-, O-(2,4-dimethyl-phenyl)-iso-butane-, O-(2,4-dimethyl-phenyl)-sec.-butane- and O-(2,4-dimethyl-phenyl)-tert.-butane- thionophosphonic acid monoester chlorides.

In addition, the mercaptans (VII) to be used as starting materials are known and can readily be prepared industrially. The following may be mentioned as specific examples thereof: methyl-, ethyl-, n-propyl-, iso-propyl-, n-butyl-, iso-butyl-, sec.-butyl-, tert.-butyl-, chloro-methyl-, 2-chloroethyl-, 3-chloro-n-propyl-, allyl-, propenyl-, propynyl- and butynyl-mercaptan.

Process variants (A), (B) and (C) are preferably carried out in the presence of suitable solvents or diluents. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, di-butyl ether and dioxane, ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 120° C., preferably at from 35° to 70° C. in the case of process variants (A) and (B) and at from 0° to 30° C. in the case of process variant (C).

In general, the reaction is allowed to take place under normal pressure.

To carry out process variant (A), the starting components are preferably employed in equimolar amounts. An excess of one or the other component produces no significant advantages. The reactants are in most cases brought together in a solvent in the presence of an acid acceptor at an elevated temperature and after completion of the reaction are worked up in the usual manner by pouring into water, extracting by shaking with an organic solvent, for example toluene, separating off the organic phase, washing, drying and distilling off the solvent.

In process variant (B), the phosphonic acid derivative is preferably employed in its salt form, in up to 10% molar excess over the halide. Here again, the reaction is generally carried out in an organic solvent and after completion of the reaction the solution is worked up in the usual manner by extraction by shaking with an organic solvent, such as, for example, toluene.

In carrying out process variant (C), the mercaptan is preferably employed in slight excess. The reaction is preferably carried out in a solvent in the presence of an acid acceptor, at the stated temperatures. Working up is carried out in the manner described in connection with the other methods.

The compounds of the formula (I) are obtained in the form of oils which, in a number of cases, cannot be distilled without decomposition but are freed from the last volatile constituents by so-called "incipient distillation", that is to say by prolonged heating under reduced pressure to moderately elevated temperatures, and are purified in this manner. They are characterized by the refractive index.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae and ticks.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from he order of the Thysanoptera, for example *Hercinothrips femoralis* and *Thrips tabaci;* from the order of the Heteroptera, for example Eurygaster spp., *Dysdercus intermedius, Piesma quadrata; Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata legens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cocoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by anthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

The preparation of the novel compounds is shown in the following illustrative examples:

EXAMPLE 1 [Process variant (A)]

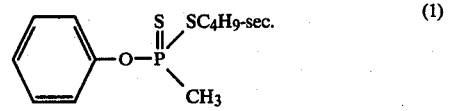

(a) S-alkyl-thionothiolphosphonic acid ester chlorides to be used as starting materials in process variant (A) were synthesized as follows:

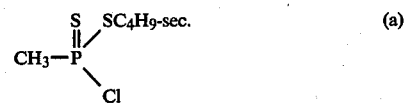

(i) Method A

A mixture of 225 g (2.5 mol) of sec.-butylmercaptan and 200 g (2.5 mol) of pyridine was added dropwise in the course of 30 minutes, while stirring, to a solution of 292.4 g (2.5 mol) of methyldichlorophosphine in 1,600 ml of dry toluene at −20° C. Stirring was then continued for 30 minutes at −20° C., the temperature was allowed to rise to room temperature in the course of one hour, and 80 g (2.5 mol) of finely powdered flowers of sulphur were introduced into the reaction solution at 30° C. The reaction mixture was then warmed to 90° C. for one hour, after which it was boiled for half an hour under reflux. After cooling to 25° C., the mixture was filtered, the filtrate was concentrated in vacuo on a rotary evaporator and the residue was distilled. 240 g (47% of theory) of S-sec.-butyl-thionothiolmethanephosphonic acid ester chloride of boiling point 95° C./4 mm Hg remained.

(ii) Method B

A mixture of 9 g (0.1 mol) of sec.-butylmercaptan and 18.0 g (0.1 mol) of pyridine was added dropwise, while stirring, to a solution of 14.8 g (0.1 mol) of methanethionophosphonic acid dichloride in 150 ml of toluene at 10° C. Thereafter the reaction solution was warmed for 10 hours to 80° C. and was then cooled to room temperature and filtered. The filtrate was concentrated in vacuo on a rotary evaporator and the residue was distilled. 16 g (80% of theory) of S-sec.-butyl-thionothiolmethanephosphonic acid ester chloride of boiling point 95° C./4 mm Hg remained.

The following compounds of the formula

could be prepared analogously:

Table 1

| Intermediate | R | $R^1$ | Method | Yield (% of theory) | Boiling point °C./mm Hg |
|---|---|---|---|---|---|
| b | $C_4H_9$-sec. | $C_2H_5$ | A | 82 | 100/4 |
| c | $C_3H_7$-n | $CH_3$ | A | 52 | 100/7 |
|   |            |         | B | 65 | 97/5 |
| d | $C_2H_5$ | $C_2H_5$ | A | 64 | 82/3 |
| e | $CH_3$ | $CH_3$ | A | 52 | 65/6 |

(b) A mixture of 9.4 g (0.1 mol) of phenol, 16.8 g (0.12 mol) of potassium carbonate and 250 ml of acetonitrile was stirred for 2 hours at 50° C. and 20.25 g (0.1 mol) of S-sec.-butyl-methanethionothiolphosphonic acid ester chloride were then added dropwise. After stirring for two hours at 50° C., the reaction solution was shaken with 200 ml of water and 400 ml of toluene and the mixture was separated in a separating funnel. The organic phase was dried over magnesium sulphate and after filtration the toluene was stripped off in vacuo on a rotary evaporator. 25 g (96% of theory) of S-sec.-butyl-O-phenyl-thionothiolmethanephosphonic acid ester remained in the form of a colorless oil having a refractive index $n_D^{22}$ of 1.5681.

EXAMPLE 2 [Process variant (B)]

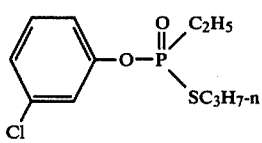

(2)

(a)

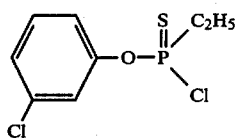

A solution of 1.29 kg (10 mol) of 3-chlorophenol and 0.4 kg (10 mol) of sodium hydroxide in 1.7 liters of water was added dropwise to 1.79 kg (1 mol) of ethanethionophosphonic acid dichloride in the course of 2 to 3 hours at 5°-10° C. After completion of the addition, the cooling was removed and the mixture was stirred for a further 10 to 12 hours at room temperature. Thereafter, the reaction mixture was diluted with 10 liters of water and extracted with 10 liters of toluene. The toluene solution was dried over sodium sulphate and then concentrated. The residue was subjected to incipient distillation at 100° C./2 mm Hg. 2.3 kg (82% of theory) of O-(3-chloro-phenyl)-thionoethanephosphonic acid ester chloride were obtained in the form of a light yellow oil.

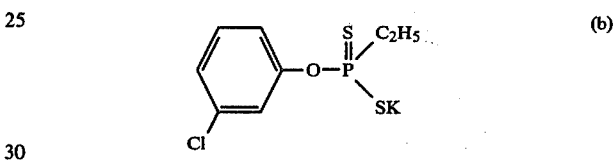

(b)

318 g (9.35 mol) of hydrogen sulphide were passed into a suspension of 2.67 kg (19.3 mol) of potassium hydroxide in 14 liters of acetonitrile at −15° C. 2.3 kg (9 mol) of O-(3-chloro-phenyl)-thionoethanephosphonic acid ester chloride were added dropwise in the course of 1 to 2 hours, the temperature was allowed to rise to 20° C. and the mixture was stirred for 12 hours at 20° C. Hydrogen sulphide was then passed in once more until the reaction was complete. The excess hydrogen sulphide was then removed in vacuo, the reaction mixture was filtered and the filtrate was concentrated in vacuo. 2.6 kg (99% of theory) of the potassium salt of O-(3-chloro-phenyl)-thionothiolethanephosphonic acid ester were obtained in the form of beige-colored crystals.

(c) 0.615 kg (5 mol) of n-propyl bromide were added dropwise to a suspension of 1.6 kg (5.4 mol) of the potassium salt of O-(3-chlorophenyl)-thionothiolethanephosphonic acid ester in 5 liters of acetonitrile at 45° C., during which addition the temperature rose to 55° C. The reaction mixture was stirred for a further 24 hours at 20°-25° C. and was poured into 6 liters of toluene, and the toluene solution was washed twice with 6 liters of water at a time, dried over sodium sulphate and then concentrated. The residue was subjected to incipient distillation at 80° C. and 2 mm Hg. 1.31 kg (82% of theory) of S-n-propyl-O-(3-chloro-phenyl)-thionothiolethanephosphonic acid ester were obtained in the form of a yellow oil having a refractive index $n_D^{25}$ of 1.5812.

EXAMPLE 3 [Process variant (C)]

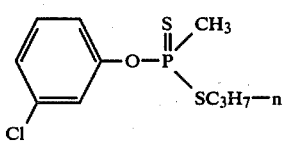

(3)

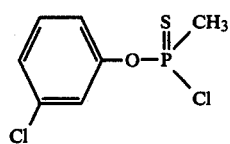

A solution of 20 g (0.5 mol) of sodium hydroxide and 64.25 g (0.5 mol) of 3-chloro-phenol was added dropwise in the course of 2 hours to 74.5 g (0.5 mol) of thionomethanephosphonic acid dichloride at about 10° C. The reaction was then allowed to continue for 15 hours at 20°–25° C., after which the reaction mixture was poured into 0.5 liter of toluene. The toluene solution was washed twice with ice-water, dried over sodium sulphate and then concentrated. After incipient distillation, 75 g (63% of theory) of O-(3-chlorophenyl)-thionomethanephosphonic acid ester chloride were obtained in the form of a yellow oil having a refractive index $n_D^{27}$ of 1.5808.

(b) 24.1 g (0.1 mol) of O-(3-chloro-phenyl)-thionomethanephosphonic acid ester chloride were added dropwise in the course of 30 minutes to a solution of 8.1 g (0.12 mol) of sodium ethylate and 9 g (0.115 mol) of n-propylmercaptan in 50 ml of ethanol, at 0°–5° C. The reaction mixture was stirred for a further 2 hours at 20°–25° C. and was then poured into 250 ml of toluene. The toluene solution was washed with 5% strength sodium carbonate solution and water, dried over sodium sulphate and then concentrated. After incipient distillation, 20 g (72% of theory) of S-n-propyl-O-(3-chlorophenyl)-thionothiolmethanephosphonic acid diester were obtained in the form of a yellow oil having a refractive index $n_D^{28}$ of 1.5721.

The following compounds of the formula

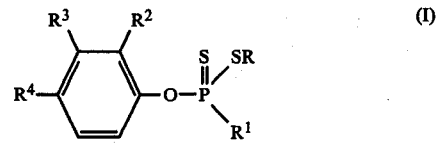

could be synthesized analogously:

TABLE 2

| Compound | R | $R^1$ | $R^2$ | $R^3$ | $R^4$ | Yield (% of theory) | Process Variant | Refractive index: |
|---|---|---|---|---|---|---|---|---|
| 4 | $C_4H_9$-sec. | $CH_3$ | $OCH_3$ | H | H | 86 | A | $n_D^{23}$:1.5620 |
| 5 | $C_3H_7$-n | $C_2H_5$ | $OCH_3$ | H | H | 82 | B | $n_D^{18}$:1.5728 |
| 6 | $CH_3$ | $CH_3$ | $OCH_3$ | H | H | 86 | B | $n_D^{22}$:1.5988 |
| 7 | $CH_3$ | $C_2H_5$ | $OCH_3$ | H | H | 84 | B | $n_D^{22}$:1.5918 |
| 8 | $C_4H_9$-sec. | $CH_3$ | H | H | $C_4H_9$-tert. | 72 | A | $n_D^{25}$:1.5420 |
| 9 | $C_4H_9$-sec. | $CH_3$ | CN | H | Br | 84 | A | $n_D^{20}$:1.5790 |
| 10 | $C_4H_9$-sec. | $CH_3$ | $CH_3$ | H | H | 76 | A | $n_D^{23}$:1.5598 |
| 11 | $C_4H_9$-sec. | $C_2H_5$ | $C_4H_9$-tert. | H | H | 81 | A | $n_D^{20}$:1.5520 |
| 12 | $C_4H_9$-sec. | $C_2H_5$ | $C_3H_7$-iso | H | H | 93 | A | $n_D^{20}$:1.5496 |
| 13 | $C_3H_7$-n | $C_2H_5$ | $C_2H_5$ | H | H | 86 | B | $n_D^{18}$:1.5637 |
| 14 | $C_4H_9$-sec. | $C_2H_5$ | (phenyl) | H | H | 72 | A | $n_D^{20}$:1.6002 |
| 15 | $C_4H_9$-sec. | $CH_3$ | H | $OCH_3$ | H | 67 | A | $n_D^{23}$:1.5630 |
| 16 | $C_4H_9$-sec. | $CH_3$ | H | Cl | H | 91 | A | $n_D^{24}$:1.5667 |
| 17 | $C_2H_5$ | $C_2H_5$ | H | Cl | H | 78 | C | $n_D^{26}$:1.5792 |
| 18 | $C_4H_9$-sec. | $CH_3$ | Cl | H | Cl | 69 | A | $n_D^{20}$:1.5740 |
| 19 | $C_3H_7$-iso | $CH_3$ | Cl | H | Cl | 44 | B | $n_D^{21}$:1.5913 |
| 20 | $C_4H_9$-n | $CH_3$ | Cl | H | Cl | 61 | B | $n_D^{21}$:1.5827 |
| 21 | $C_4H_9$-iso | $CH_3$ | Cl | H | Cl | 36 | B | $n_D^{21}$:1.5780 |
| 22 | $C_3H_7$-n | $C_2H_5$ | H | H | $CH_3$ | 81 | C | $n_D^{28}$:1.5605 |
| 23 | $CH_2-CH=CH_2$ | $C_2H_5$ | H | H | H | 73 | B | $n_D^{22}$:1.5880 |
| 24 | $C_3H_7$-iso | $C_2H_5$ | H | H | H | 37 | B | $n_D^{22}$:1.5695 |
| 25 | $-CH_2-C\equiv CH$ | $C_2H_5$ | H | H | H | 63 | B | $n_D^{22}$:1.5985 |
| 26 | $CH_2-CH_2-Cl$ | $C_2H_5$ | H | H | H | 44 | B | $n_D^{22}$:1.5916 |
| 27 | $-(CH_2)_3-Cl$ | $C_2H_5$ | H | H | H | 78 | B | $n_D^{22}$:1.5860 |
| 28 | $CH_2-Cl$ | $C_2H_5$ | H | H | H | 51 | B | $n_D^{22}$:1.6066 |
| 29 | $C_3H_7$-n | $C_2H_5$ | H | H | H | 56 | B | $n_D^{22}$:1.5735 |
| 30 | $CH_2Cl$ | $CH_3$ | H | H | H | 36 | B | $n_D^{23}$:1.5920 |
| 31 | $CH_2Cl$ | $C_2H_5$ | H | Cl | H | 27 | B | $n_D^{23}$:1.6018 |
| 32 | $-CH_2-C\equiv CH$ | $CH_3$ | H | Cl | H | 77 | B | $n_D^{23}$:1.6081 |
| 33 | $CH_2Cl$ | $CH_3$ | H | Cl | H | 46 | B | $n_D^{23}$:1.6154 |
| 34 | $C_3H_7$-n | $CH_3$ | H | H | Cl | 83 | A | $n_D^{20}$:1.5850 |
| 35 | $C_4H_9$-sec. | $CH_3$ | H | H | Cl | 90 | A | $n_D^{25}$:1.5640 |
| 36 | $C_4H_9$-sec. | $CH_3$ | Cl | H | H | 85 | A | $n_D^{23}$:1.5609 |
| 37 | $C_3H_7$-n | $C_2H_5$ | Cl | H | H | 85 | B | $n_D^{19}$:1.5783 |
| 38 | $C_3H_7$-n | $CH_3$ | $SCH_3$ | H | H | 74 | A | $n_D^{23}$:1.5849 |
| 39 | $C_4H_9$-sec. | $CH_3$ | H | H | $NO_2$ | 73 | A | $n_D^{20}$:1.5870 |
| 40 | $C_4H_9$-sec. | $CH_3$ | $NO_2$ | H | H | 99 | A | $n_D^{24}$:1.5698 |
| 41 | $C_4H_9$-sec. | $CH_3$ | H | H | CN | 91 | A | $n_D^{23}$:1.5628 |
| 42 | $C_4H_9$-sec. | $CH_3$ | CN | H | H | 92 | A | $n_D^{24}$:1.5621 |
| 43 | $C_3H_7$-n | $CH_3$ | CN | H | H | 86 | A | $n_D^{26}$:1.5810 |
| 44 | $C_4H_9$-sec. | $CH_3$ | H | H | $OCH_3$ | 98 | A | $n_D^{25}$:1.5610 |
| 45 | $C_4H_9$-sec. | $CH_3$ | H | H | $SCH_3$ | 76 | A | $n_D^{20}$:1.5870 |
| 46 | $C_4H_9$-sec. | $CH_3$ | H | H | $CH_3-SO_2$ | 90 | A | $n_D^{25}$:1.5780 |
| 47 | $C_4H_9$-sec. | $CH_3$ | $CH_3$ | H | $CH_3$ | 94 | A | $n_D^{25}$:1.5430 |
| 48 | $C_3H_7$-iso | $C_2H_5$ | $CO-OC_3H_7$-iso | H | H | 45 | B | $n_D^{25}$:1.5404 |

TABLE 2-continued

| Compound | R | R¹ | R² | R³ | R⁴ | Yield (% of theory) | Process Variant | Refractive index: |
|---|---|---|---|---|---|---|---|---|
| 49 | $CH_2Cl$ | $C_2H_5$ | $CO-OC_3H_7$-iso | H | H | 35 | B | $n_D^{25} 1.5618$ |

The insecticidal, acaricidal and nematicidal activity of the present compounds of this invention is illustrated by the following examples wherein the compounds according to the present invention are each identified by the number (given in brackets) from the preparative examples hereinabove.

The known comparison compounds are identified as follows:

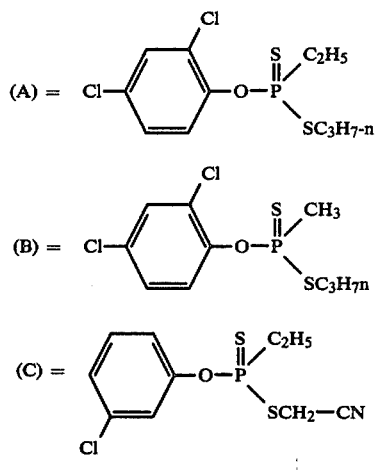

EXAMPLE 4

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/1), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 3

(Nematicides)
*Meloidogyne incognita*

| Active compounds | Degree of destruction in % at an active compound concentration of 5ppm |
|---|---|
| (A) | 0 |
| (B) | 0 |
| (19) | 100 |
| (21) | 100 |
| (37) | 100 |
| (13) | 100 |
| (17) | 100 |
| (2) | 100 |
| (3) | 100 |
| (28) | 100 |
| (29) | 100 |
| (30) | 100 |
| (43) | 100 |
| (1) | 100 |
| (35) | 100 |
| (16) | 100 |
| (34) | 100 |
| (10) | 100 |
| (36) | 100 |
| (38) | 100 |

EXAMPLE 5

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/1). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 4

(Soil insecticides)
*Tenebrio molitor* larvae in the soil

| Active compounds | Degree of destruction in % at an active compound concentration of 10 ppm |
| --- | --- |
| (A) | 0 |
| (B) | 0 |
| (49) | 100 |
| (7) | 100 |
| (6) | 100 |
| (23) | 100 |
| (24) | 100 |
| (25) | 100 |
| (26) | 100 |
| (27) | 100 |
| (28) | 100 |
| (31) | 62 |

EXAMPLE 6

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 5

(Soil insecticides)
*Phorbia antiqua* grubs in the soil

| Active compounds | Degree of destruction in % at an active compound concentration of 10 ppm |
| --- | --- |
| (A) | 0 |
| (B) | 0 |
| (17) | 100 |
| (2) | 100 |
| (3) | 100 |
| (18) | 100 |
| (45) | 100 |
| (42) | 100 |
| (1) | 100 |
| (16) | 100 |

EXAMPLE 7

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 6

(Mites which damage plants)
Tetranychus Test

| Active compounds | Active compound concentration in % | degree of destruction in % after 2 days |
| --- | --- | --- |
| (C) | 0.1 | 80 |
|  | 0.01 | 0 |
| (29) | 0.1 | 100 |
|  | 0.01 | 99 |
| (37) | 0.1 | 100 |
|  | 0.01 | 99 |
| (2) | 0.1 | 100 |
|  | 0.01 | 99 |
| (3) | 0.1 | 100 |
|  | 0.01 | 100 |
| (34) | 0.1 | 100 |
|  | 0.01 | 100 |
| (38) | 0.1 | 100 |
|  | 0.01 | 85 |
| (43) | 0.1 | 99 |
|  | 0.01 | 95 |
| (19) | 0.1 | 100 |
|  | 0.01 | 99 |
| (20) | 0.1 | 100 |
|  | 0.01 | 100 |
| (21) | 0.1 | 100 |
|  | 0.01 | 100 |
| (1) | 0.1 | 100 |
|  | 0.01 | 100 |
| (45) | 0.1 | 100 |
|  | 0.01 | 100 |
| (46) | 0.1 | 100 |
|  | 0.01 | 99 |
| (4) | 0.1 | 100 |
|  | 0.01 | 80 |
| (15) | 0.1 | 100 |
|  | 0.01 | 90 |
| (36) | 0.1 | 100 |
|  | 0.01 | 98 |
| (35) | 0.1 | 100 |
|  | 0.01 | 99 |
| (18) | 0.1 | 100 |
|  | 0.01 | 99 |
| (42) | 0.1 | 100 |
|  | 0.01 | 90 |
| (41) | 0.1 | 100 |
|  | 0.01 | 100 |
| (40) | 0.1 | 99 |
|  | 0.01 | 90 |
| (39) | 0.1 | 100 |
|  | 0.01 | 100 |
| (9) | 0.1 | 100 |
|  | 0.01 | 90 |

EXAMPLE 8

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all of the caterpillars were killed whereas 0% meant that none of the caterpillars were killed.

The active compounds, the concentrations of the active compounds, the evaluation times and the results can be seen from the following table:

Table 7

| Active compounds | (insects which damage plants) Plutella Test | |
|---|---|---|
| | Active compound concentration in % | Degree of destruction in % after 3 days |
| (A) | 0.01 | 100 |
| | 0.001 | 0 |
| (B) | 0.01 | 100 |
| | 0.001 | 0 |
| (30) | 0.01 | 100 |
| | 0.001 | 100 |
| (33) | 0.01 | 100 |
| | 0.001 | 90 |
| (28) | 0.01 | 100 |
| | 0.001 | 100 |
| (26) | 0.01 | 100 |
| | 0.001 | 100 |
| (25) | 0.01 | 100 |
| | 0.001 | 100 |
| (10) | 0.01 | 100 |
| | 0.001 | 100 |
| (36) | 0.01 | 100 |
| | 0.001 | 100 |
| (42) | 0.01 | 100 |
| | 0.001 | 100 |
| (41) | 0.01 | 100 |
| | 0.001 | 95 |

EXAMPLE 9

Test with parasitic fly larvae
Emulsifier: 80 parts by weight of Cremophor EL

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction in % was determined. 100% meant that all of the larvae had been killed and 0% meant that none of the larvae had been killed.

The active compound, amounts used and results can be seen from the table which follows:

Table 8

| | (parasitic fly larvae/*Lucillia cuprina* res.) | |
|---|---|---|
| Active compound | Active compound concentration in ppm | Destructive action in % |
| (5) | 100 | 100 |
| | 30 | 100 |
| | 10 | 100 |
| | 3 | 0 |
| (17) | 100 | 100 |
| | 30 | 100 |
| | 10 | >50 |
| | 3 | 0 |
| (21) | 100 | 100 |
| | 10 | 100 |
| | 1 | 0 |

EXAMPLE 10

Test with parasitic scab mites (*Psoroptes cuniculi*)
Solvent: Cremophor

To produce a suitable preparation of active compound, the active substance in question was mixed with the stated solvent in the ratio of 1:2 and the concentrate thus obtained was diluted with water to the desired concentration.

About 10–25 scab mites (*Psoroptes cuniculi*) were introduced into 1 ml portions of the active compound preparation to be tested, which had been pipetted into the tablet nests of a blister pack. After 24 hours, the degree of destruction in percent was determined. 100% meant that all of the mites had been killed and 0% meant that none of the mites had been killed.

Active compounds, active compound concentrations and results can be seen from the table which follows:

Table 9

| | (parasitic scab mites/*Psoroptes cuniculi*) | |
|---|---|---|
| Active compound | Active compouund concentration in ppm | Destructive action |
| (5) | 100 | 100 |
| | 30 | 100 |
| | 10 | 100 |
| | 3 | 0 |
| (21) | 1000 | 100 |
| | 100 | 100 |
| | 10 | — |

It will be appreciated that the instant specification and examples are set forth by way of illustration and not limitation, and that various modifications and changes may be made without departing from the spirit and scope of the present invention.

What is claimed is:

1. An O-phenyl-thionothiolalkanephosphonic acid ester of the formula

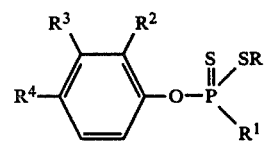

R is butyl, or alkenyl or halogenoalkyl each with up to 6 carbon atoms,
$R^1$ is alkyl with 1 to 6 carbon atoms,
$R^2$ is hydrogen, cyano, nitro, chlorine, bromine, phenyl, or alkyl, carbalkoxy, alkoxy or alkylthio each with 1 to 4 carbon atoms in the alkyl or alkoxy moiety, R³ is hydrogen, chlorine, methoxy or ethoxy, and R⁴ is hydrogen, chlorine, cyano, nitro, methoxy, ethoxy, methylthio, ethylthio, methylsulphonyl, ethylsulphonyl or alkyl with 1 to 4 carbon atoms.

2. A method of combating arthropods or nematodes which comprises applying to the arthropods or nematodes, or to a habitat thereof, an arthropodicidally or nematicidally effective amount of a compound according to claim 1.

3. The method according to claim 2 in which said compound is

S-sec.-butyl-O-phenyl-thionothiolmethanephosphonic acid ester,

S-sec.-butyl-O-phenyl-thionothiolethanephosphonic acid ester,

S-β-chloroethyl-O-phenyl-thionothiolethanephosphonic acid ester or

S-chloromethyl-O-phenyl-thionothiolethanephosphonic acid ester.

4. An arthropodicidal or nematicidal composition containing as active ingredient an arthropodicidally or nematicidally effective amount of a compound according to claim 1 in admixture with a diluent.

5. A compound according to claim 1, wherein such compound is S-sec.-butyl-O-phenyl-thionothiolmethanephosphonic acid ester of the formula

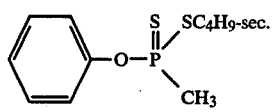

6. A compound according to claim 1, wherein such compound is S-sec.-butyl-O-phenyl-thionothiolethanephosphonic acid ester of the formula

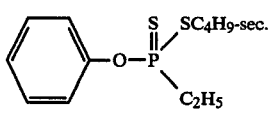

7. A compound according to claim 1, wherein such compound is S-β-chloroethyl-O-phenyl-thionothiolethanephosphonic acid ester of the formula

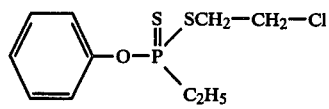

8. A compound according to claim 1, wherein such compound is S-chloromethyl-O-phenyl-thionothiolethanephosphonic acid ester of the formula

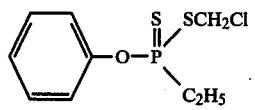

9. S-n-propyl-O-(3-chloro-phenyl)-thionothiolethanephosphonic acid ester of the formula

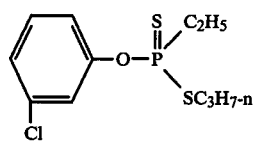

10. An arthropodicidal or nematicidal composition containing as active ingredient an arthropodicidally or nematicidally effective amount of a compound according to claim 9 in admixture with a diluent.

11. A method of combating arthropods or nematodes which comprises applying to the arthropods or nematodes, or to a habitat thereof, an arthropodicidally or nematicidally effective amount of a compound according to claim 9.

12. An S-n-propyl-O-phenyl-thionothiolethanephosphonic acid ester of the formula

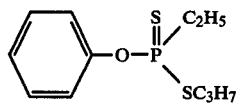

13. An arthropodicidal or nematicidal composition containing as active ingredient an arthropodicidally or nematicidally effective amount of a compound according to claim 12 in admixture with a diluent.

14. A method of combating arthropods or nematodes which comprises applying to the arthropods or nematodes, or to a habitat thereof, an arthropodicidally or nematicidally effective amount of a compound according to claim 12.

* * * * *